United States Patent [19]
Drummond et al.

[11] Patent Number: 5,620,891
[45] Date of Patent: Apr. 15, 1997

[54] BIOLOGICAL REACTION PROCESSES

[75] Inventors: Humphrey Drummond, South Windsor; Clinton Kopp, Castle Hill; Paul Khoo, Northmead; Warren Johnson, Bligh Park; Aloke Vaid, South Windsor, all of Australia

[73] Assignee: Memtec Limited, South Windsor, Australia

[21] Appl. No.: 108,713

[22] PCT Filed: Mar. 9, 1992

[86] PCT No.: PCT/AU92/00102

§ 371 Date: Aug. 8, 1994

§ 102(e) Date: Aug. 8, 1994

[87] PCT Pub. No.: WO92/15667

PCT Pub. Date: Sep. 17, 1992

(Under 37 CFR 1.47)

[30] Foreign Application Priority Data

Mar. 8, 1991 [AU] Australia .................... PK4994

[51] Int. Cl.6 .................... C12N 1/00; C12M 1/14
[52] U.S. Cl. .................... 435/243; 435/286.6; 435/299.1; 210/617; 210/150
[58] Field of Search .................... 435/3, 285, 41, 435/243, 289, 310, 313, 315, 813, 818, 262, 262.5, 286.5, 286.6, 289.1, 299.1; 210/615–618, 150, 151

[56] References Cited

U.S. PATENT DOCUMENTS

| | | | |
|---|---|---|---|
| 3,838,524 | 10/1974 | Hencke et al. | 34/9 |
| 3,928,190 | 12/1975 | Bébin | 210/8 |
| 3,933,629 | 1/1976 | Smith | 210/17 |
| 4,076,616 | 2/1978 | Verde | 210/618 |
| 4,113,613 | 9/1978 | Sekoulov et al. | 210/618 |
| 4,435,286 | 3/1984 | Louboutin et al. | 210/116 |
| 4,581,143 | 4/1986 | Pepper | 210/614 |
| 5,314,621 | 5/1994 | Rogalla | 210/618 |

FOREIGN PATENT DOCUMENTS

| | | | |
|---|---|---|---|
| 5207679 | 10/1970 | Australia. | |
| 4087688 | 3/1992 | Japan | 210/618 |
| 0587147 | 1/1978 | U.S.S.R. | |
| 1105500 | 7/1984 | U.S.S.R. | |
| 1433911 | 10/1988 | U.S.S.R. | |
| 1636445 | 3/1991 | U.S.S.R. | |
| 0971338 | 9/1964 | United Kingdom | 210/618 |
| 1406255 | 9/1975 | United Kingdom | 210/618 |

Primary Examiner—William Beisner
Attorney, Agent, or Firm—Waldron & Associates

[57] ABSTRACT

A process for maintaining a high rate of mass transfer of nutrients contained in a liquid feed stream to a biofilm of microorganisms supported on a bed of particulate matter. The microorganisms in the biofilm are subjected to a continuous, uniform flow of the liquid feed steam and a countercurrent flow of respiratory air so as to support biofilm growth. The bed is periodically pulsed with air at a pressure sufficient to shed microorganisms from the biofilm, and at intervals sufficient to avoid preferential channeling of the liquid feed steam through the bed and/or to disrupt and rearrange the bed of particulate matter.

16 Claims, 13 Drawing Sheets

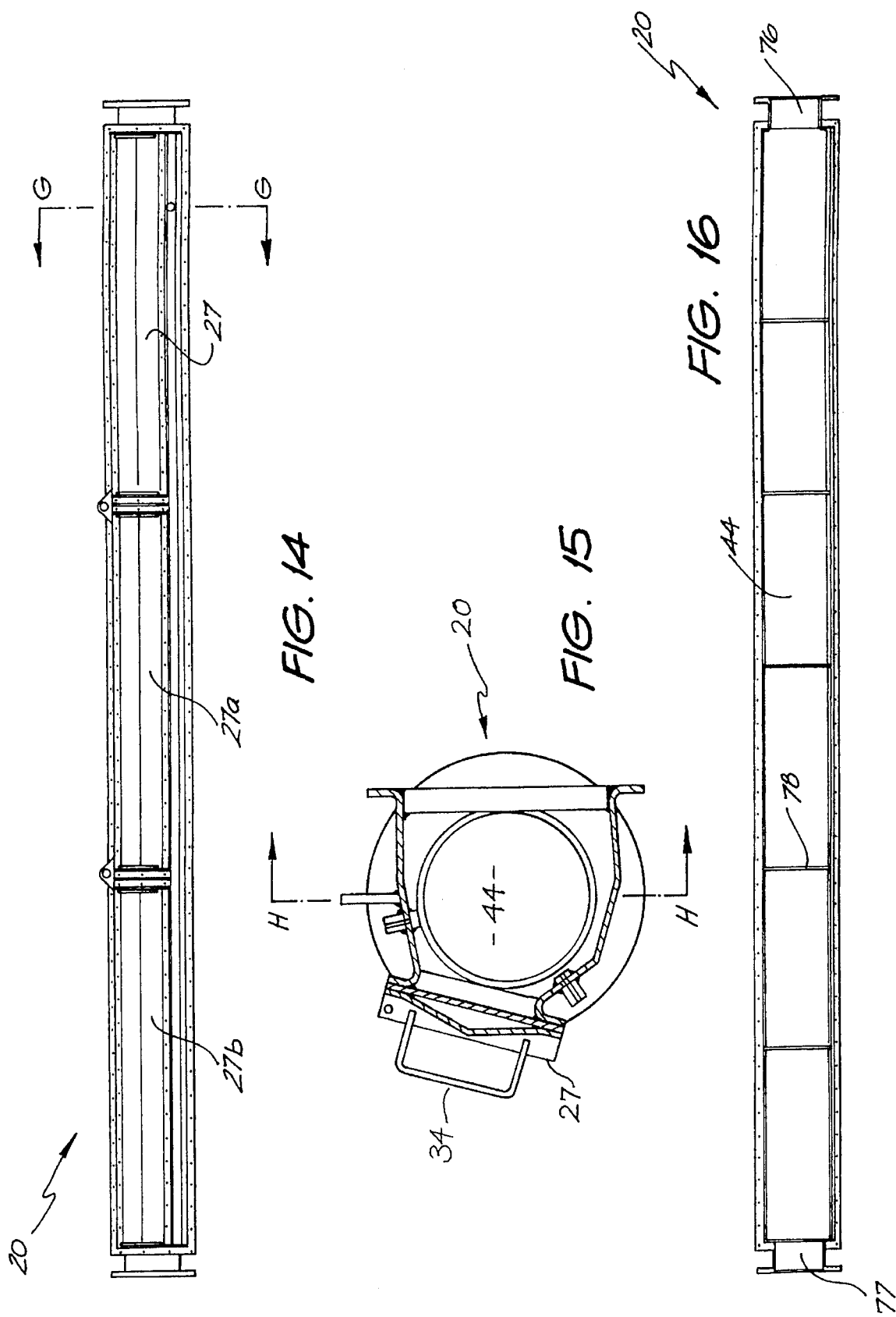

BIOLOGICAL REACTION PROCESSES

FIELD OF INVENTION

This invention relates to biological reaction processes and bioreactors for use in such processes.

Biological reaction processes are used for the production of cell mass or biomass as well as for the production of metabolites and for biological transformations. The invention is particularly concerned with such processes wherein the microorganisms used in the process are adsorbed or immobilized onto a support medium.

The biological reaction process may involve the conversion of dissolved or colloidal polluting nutrient into cell mass such as in the treatment of sewage, industrial effluent and surface water.

For the sake of brevity and convenience, the invention will be described in relation to a biological reaction process involving the production and utilization of cell mass for treating a liquid feed such as sewage or industrial effluent so as to reduce substantially or eliminate the polluting capacity of that sewage or effluent. However, it is to be understood that the invention is not limited to the treatment of sewage or industrial effluent as it may be applied to other feeds and to other biological reaction processes in which microorganisms used in the process are adsorbed or immobilized or otherwise supported onto a support medium. The microorganisms (such as bacteria, fungi, algae and protozoa) are preferably derived from the sewage and digest nutrient that is also present in the sewage. This nutrient may contain carbonaceous material and can be in solid or soluble form, and is quantifiable in the art as Biological Oxygen Demand (BOD) and Chemical Oxygen Demand (COD). The biological reaction process can be used to remove nitrogen from sewage by conversion to nitrates.

BACKGROUND ART

Prior art biological reaction processes for the treatment of sewage suffer from the disadvantage, to varying degrees, of low efficiency in terms of the amount of resources required and the time taken to process a given volume of sewage.

Attempts to increase the efficiency of known biological reactions processes for the treatment of sewage have focused on various parameters of these types of reaction processes including the means for distribution of respiratory air to the reaction vessel; techniques for the reorientation of the support medium to prevent channelling and to introduce greater flow of air and liquid through the support medium; the nature of the support medium; and methods of controlling the air and liquid delivery rates to the system.

For example, Australian Patent Specification 528,760 describes a process for purifying polluted water by percolating it downwardly through a submerged, fixed granular bed. Oxygenated gas is fed upwardly from an intermediate level of the bed and treated water is discharged from the bottom of the bed. The flow of water to be treated and the flow of the oxygenated gas is adjusted in such a way that specific mathematical relationships are satisfied.

In the process described in the Australian Specification 528,760, the critical parameters for efficient operation are said to be the rate of flow of water to be treated over the granular bed and the volume of oxygen supplied to the microorganisms. Of these two parameters, regulation of the dissolved oxygen content of the water is the key to maintaining the process at its optimum rate.

In order to achieve acceptable results with this process, it is necessary to take the water through several pre- and post-treatment stages including pre-oxidation with ozone and filtration through sand.

The process described in Australian Specification 528,760 is described in an article by Barr K. G. in the journal *Water* of March 1988. In that process, it is intended that the water flow/oxygenated gas flow mathematical relationships achieve high concentrations of biomass growth on the granular bed to allow high loading rates or low hydraulic retention times.

Prior art processes for the treatment of sewage or polluted water have made a number of assumptions regarding the fundamental nature of the biological reaction process. All these prior art processes, including that of Australian specification 528,760, assumed that there is a requirement for a large mass of microorganisms in order to establish a large biofilm density to achieve increased rates of conversion of nutrients to the desired product.

There has also been an assumption that the nutrient and environmental requirements (such as optimal concentration of dissolved oxygen to all parts of the system) of the microbial species play a significant part in the efficient operation of the process.

The various elements of known biological reaction processes have all received investigation on the basis of the desirability for a large amount of biofilm which is thought to result in the highest rates of conversion and to efficient operation.

In particular, prior art processes have, in the main, tended towards finding ways of increasing biofilm quantity.

The improved processes arising from those investigations have met with varying degrees of success such that the more successful processes exhibit high efficiencies in the initial stages of operation only.

However, the nature of the improvements to date have been such that these prior art processes have not been able to maintain the high level of efficiency for prolonged periods. The efficiency gradually falls to unacceptable levels at which point the plant is shutdown in order that backwashing, cleaning, maintenance and other steps may be taken to restore the process to its initial high efficiency.

The reason for the fall in efficiency is thought to be due to the excessively large quantity of biofilm or thick biofilm created by the process which clogs the system and leads to deleterious channelling effects in the process vessel or bioreactor.

Research by the applicant has surprisingly shown that the uninterrupted growth of thick biofilms over long periods of time do not lead to the highest conversion rates but to greater inefficiencies in biological reaction processes.

It has not been found by the present inventors that the highest conversion rate of nutrients and the highly efficient operation of the processes of the invention can be achieved through interrupting the growth of biofilm more frequently than is carried out in the prior art, and particularly in AU 528,760 and that this high efficiency can be maintained for an equally large mass of biofilm as long as the particles chosen for the support medium are of an optimal size.

An object of the invention is to keep the rate of mass transfer of nutrients to the microorganisms as high as possible. This is achieved largely by minimising the detrimental effects of channelling of nutrient and air through the process vessel or bioreactor.

The mass transfer system of the invention involves the movement of dissolved oxygen and other nutrients from the liquid feed to the biofilm and the removal of products of the biological reaction process. This process can be defined as follows:

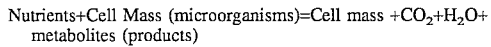
Nutrients+Cell Mass (microorganisms)=Cell mass $+CO_2+H_2O+$ metabolites (products)

A high rate of mass transfer of nutrients is achieved by providing periodic pulses of air through the bioreactor to disrupt the bed of support particles and remove any localized clogging of solid matter in the bed that may lead to channelling of nutrient away from metabolically potent cell mass.

The periodic pulses are preferably of an explosive nature sufficient to disrupt the bed of support particles.

The achievement of a high rate of mass transfer of nutrients is assisted by providing support particles in the bed of an optimal size. The smaller the effective size of the support particles, the greater is the total bed surface area available for attachment and growth of the microorganisms and, accordingly, the greater the surface area of resultant biofilm. However, as the accumulation of smaller support particles create smaller gaps between particles than would the accumulation of larger support particles, the possibility of the biofilm growing to form a bridge across adjacent small sized particles is heightened, with the effect that effective surface area of metabolically potent cell mass falls. The more frequently periodic pulsing with air through the process vessel in the present invention removes these bridges and restores the high effective surface area of metabolically potent cell mass.

In addition, the pulsing occurs at a frequency so as to control the residence time of solids in the bed.

SUMMARY OF INVENTION

According to the invention there is provided a process for maintaining a high rate of mass transfer of nutrients contained in a liquid feed stream to a biofilm of microorganisms supported on a bed of particulate matter, the process comprising feeding the microorganisms in the biofilm with a continuous, uniform flow of the liquid feed stream and a countercurrent flow of respiratory air so as to support biofilm growth, and periodically pulsing the bed with air at a pressure sufficient to shed microorganisms from the biofilm and at intervals sufficient to avoid preferential channelling of the liquid feed stream through the bed and/or to disrupt and rearrange the bed of particulate matter.

Preferably, the process is interrupted by a backwashing of the bed less frequently than the periodic pulsing.

The invention further provides a bioreactor for treating a liquid feed stream to remove nutrient BOD (biological oxygen demand) and COD (chemical oxygen demand) therefrom, comprising:
(i) a vessel containing a bed of particulate matter upon which grow a biofilm of microorganisms that remove nutrient BOD and COD,
(ii) means for passing the liquid feed stream downwardly through the bed and,
(iii) means for passing a continuous uniform flow of respiratory air and a flow of pulsed air upwardly through the bed.

Preferably, the means for passing air through the bed includes a plurality of spaced apart porous tubes from which the air passes into the bed.

Preferably, the porous tubes are made of microporous polyethylene. The particulate material can be coal, activated carbon, anthracite, zeolite or any inert particulate material that is capable of supporting microorganisms.

Preferably, the particulate material is any coal media having an effective size of 2.3 to 2.5 mm with an uniformity coefficient of 1.5. The bed of particulate matter can be either fixed or fluidized and is submerged during operation of the process.

The microorganisms suitable for this process are those that occur naturally in sewage or are present in the industrial waste water to be treated. The process streams can be inoculated with microorganisms if desired. However, inoculation of this kind is not required in most instances to achieve the high operating efficiencies of the process of the invention.

The pressure at which process or respiratory air enters the bioreactor is not critical but is preferably between 20 and 70 kPa to provide the respiratory air requirements in an economical way.

The process of the invention may be operated in a co-current way with fluidization of the support bed. In this mode of operation, the pressures of liquid and air must be sufficient to fluidize the support medium in the required manner and are generally in excess of 70 kPa.

The amount of dissolved material such as nutrients in the liquid to be treated is a significant factor in the operation of the process of the invention in as much as it effects the pulse interval and the pressure of the pulse required. Variable flow rates of the liquid to be treated do not effect the process in any significant way.

Pulsation agitates and rearranges the bed support particles thus preventing channelling and clumping of the support particles and the biomass. Pulsation also removes or sheds biomass from the support particles.

The respiratory air creates turbulence and shear forces in the narrow voids between particles of the bed as well as providing gaseous nutrient to the cell mass.

There is also the combined effect of the counter-current flow of respiratory air and the liquid to be treated which adds to the turbulence and minor agitation of the bed support particles.

The backwashing of the bioreactor vessel removes biomass shed during operation of the process and the sludge formed at the top of the bed.

Preferably, pulsation is performed at intervals of between 20 minutes and 2 hours. It is preferred that the pulsation is for 1 to 8 seconds duration. Preferably, the pressure of the pulses is in the range of 60 kPa to 120 kPa, but more preferably 70 kPa. The effect of the pulsation is explosive in nature, causing rapid disruption of the bed.

It is preferred that the backwashing of the bioreactor vessel be carried out at intervals of from 3 to 24 hours. It is further preferred that backwashing be carried out for a duration of from 3 to 7 minutes.

Preferably, the backwashing regime involves stopping the operation of the biological reaction process and pumping liquid upwardly through the bioreactor vessel at a rate sufficient to cause the support particles to lift uniformly and gently.

During the pumping of liquid, pulses of air are sent upwardly through the vessel to shed biomass from the support particles. The lighter sewage solids and shed biomass are left at the top of the vessel and are drained off with the liquid containing those solids and shed biomass.

In a particular form of the invention, the bioreactor vessel is interconnected with a continuous microfiltration unit of the type described in Australian Patents 563,321 and 576, 424 whereby all remaining solids and shed biomass are removed from the bioreactor vessel effluent by the filtration unit and the effluent is disinfected. The backwash from the continuous microfiltration unit may be recycled into the bioreactor feed.

Preferably, the liquid that is pumped upwardly during the backwash cycle is effluent from the bioreactor.

BRIEF DESCRIPTION OF THE DRAWINGS

In order that the invention may be more readily understood and put into practical effect, reference will now be made to the accompanying drawings in which:

FIG. 14 is a side elevational view of a liquid flow header for the bioreactor of FIG. 1, FIG. 15 is a sectional view taken in the direction of arrows GG of FIG. 14, FIG. 16 is a sectional view taken in the direction of arrows HH of FIG. 15.

DESCRIPTION OF THE PREFERRED EMBODIMENTS

Figure 1:
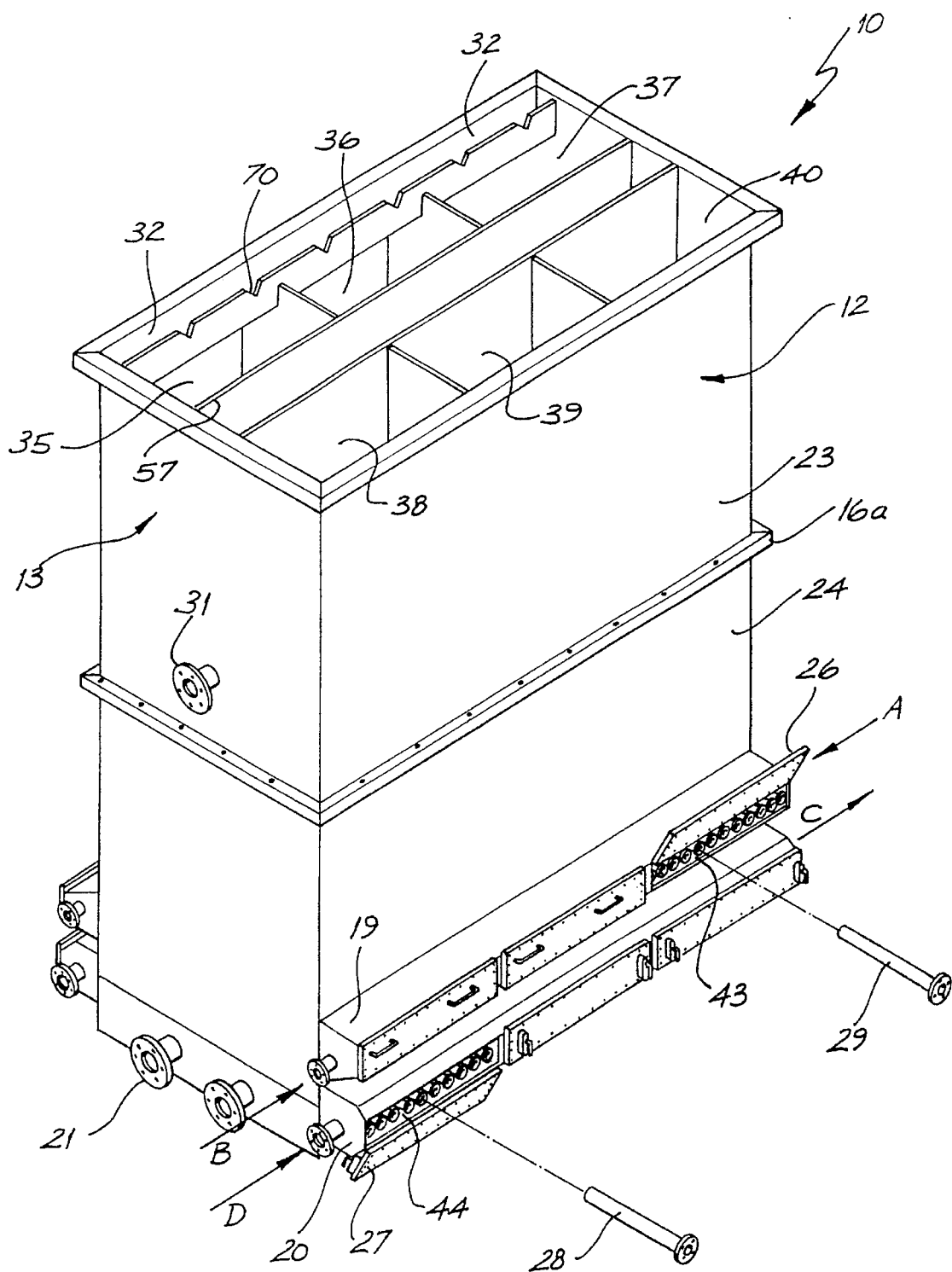
FIG. 1 is a perspective view of a bioreactor according to a preferred embodiment of the invention.
Figure 2:
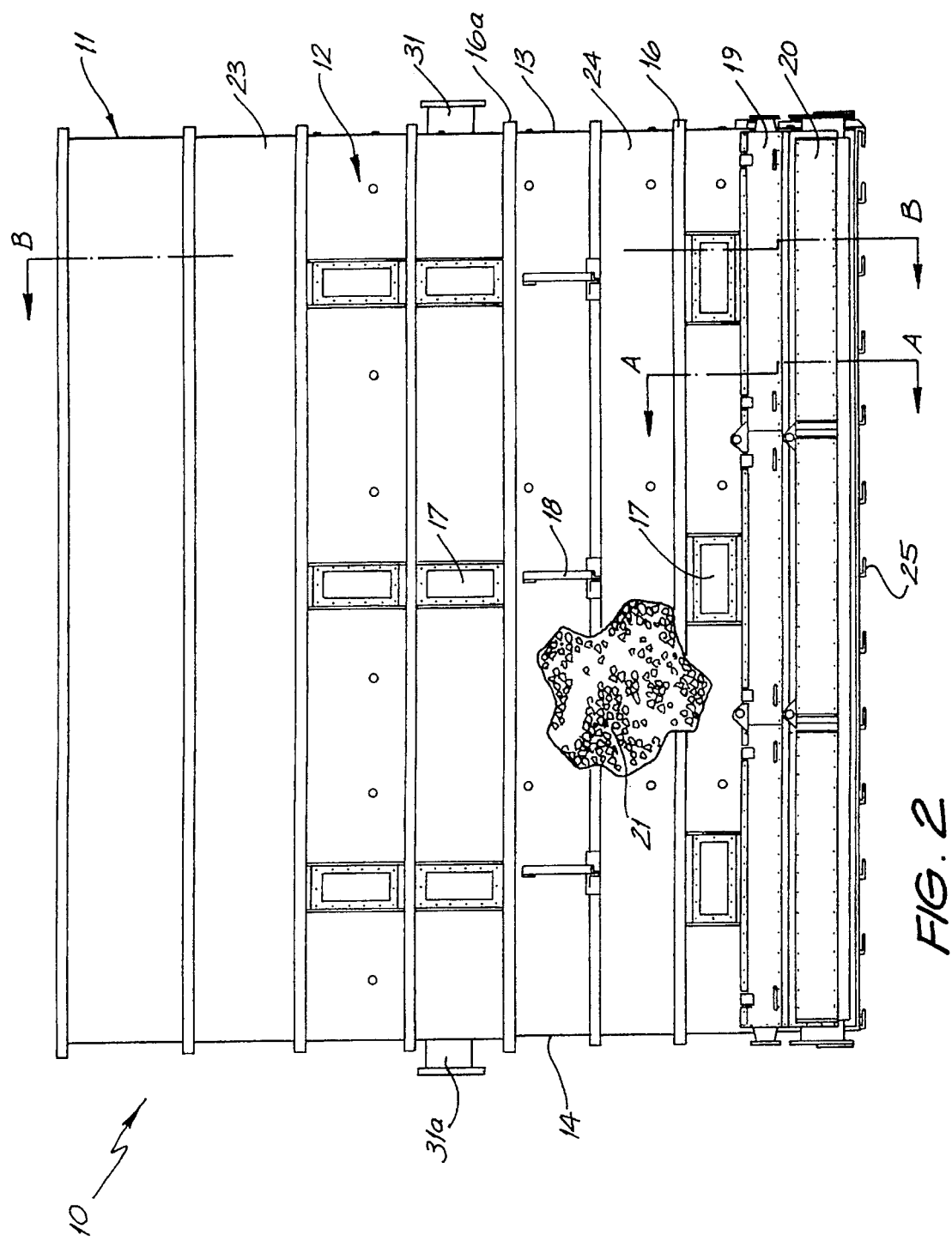
FIG. 2 is a front elevational view of the bioreactor of FIG. 1.
Figure 3:
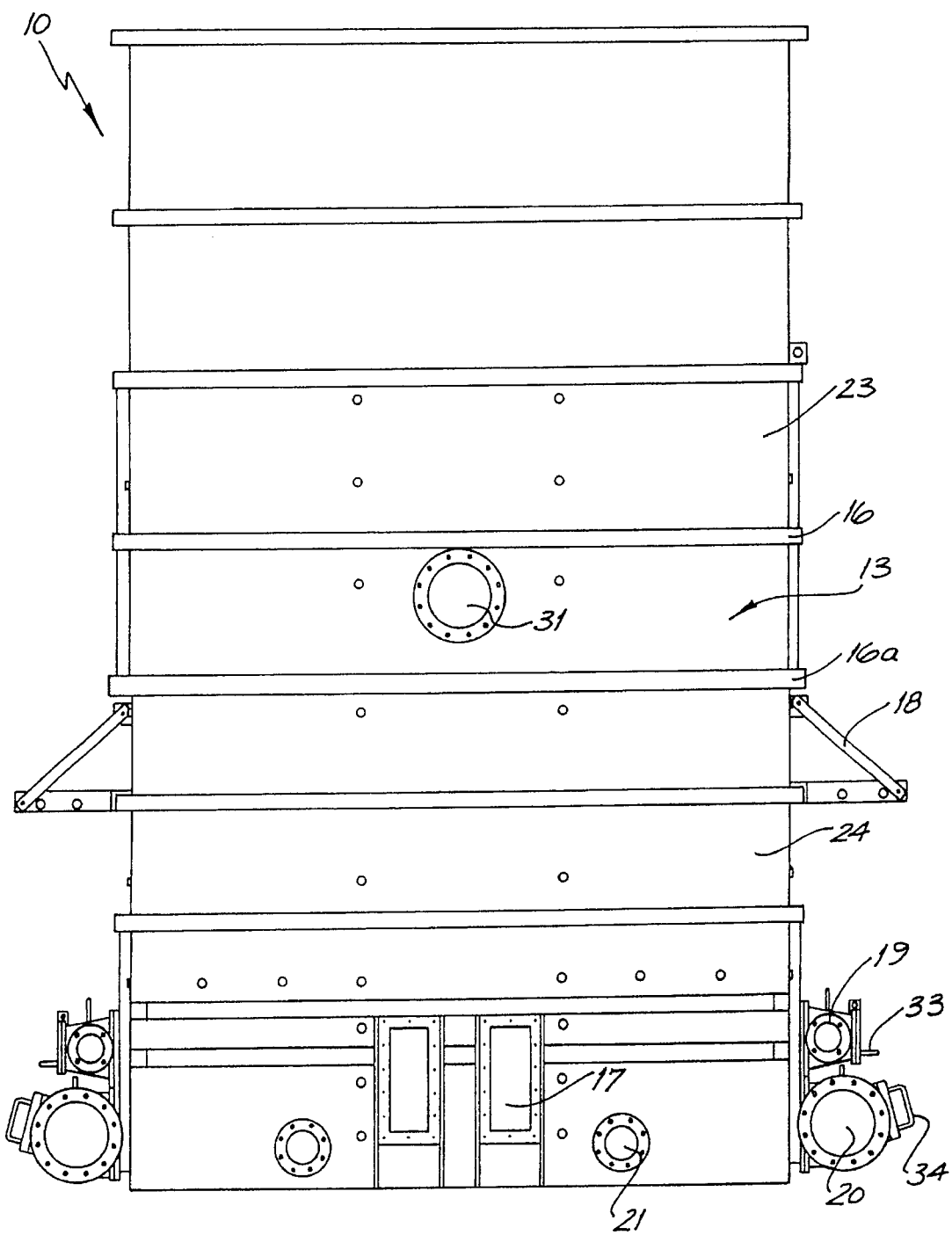
FIG. 3 is a side elevational view of the bioreactor of FIG. 1.

The bioreactor 10 shown in FIGS. 1, 2 and 3 includes a vessel 11 of rectangular prism shape having a front wall 12, two identical side walls 13 and 14 and a rear wall (not shown) identical to the front wall. Each wall has a series of stiffening flanges 16. The cross-sectional area of the vessel 11 is, in this instance, approximately 20 square meters.

The vessel 11 has sight glasses 17 for visual inspection of the interior of the vessel 11 and lifting beams 18 on its front, side and rear walls.

During normal operation of the bioreactor 10, air is supplied to the interior of the vessel 11 through air supply headers 19, that extend along the front and rear walls, and liquid is withdrawn from the interior of the vessel 11 through liquid flow headers 20 also extending along the front and rear walls. The headers 19 and 20 have hinged covers 26 and 27 for access to the main header air supply tube 43 and main header liquid flow tube 44 therewithin. Handles 33 and 34 facilitate the opening of the covers 26 and 27.

Located within the vessel 11 is a packed bed of coal particles 21 (shown in part through a removed portion of the front wall 12 in FIG. 2) of effective size between 2.3 and 2.5 mm with a uniformity co-efficient of 1.5. The bed particles 21 rest on the floor 22 of the vessel 11.

Figure 6:
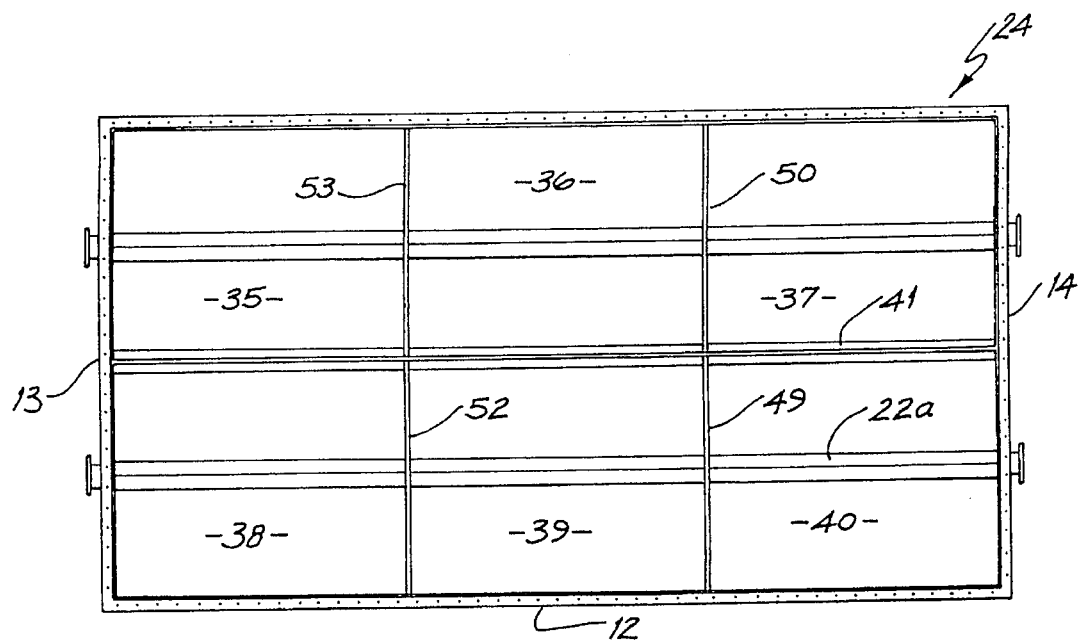
FIG. 6 is a plan view of the bottom section of the bioreactor of FIG. 1.
Figure 7:
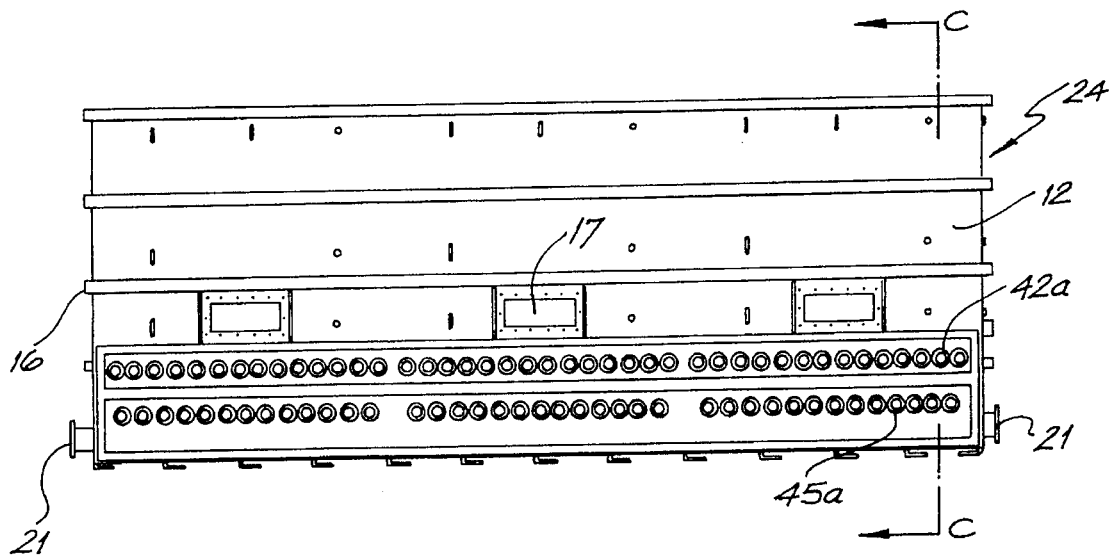
FIG. 7 is a front elevational view of the bottom section of the bioreactor of FIG. 1.
Figure 10:
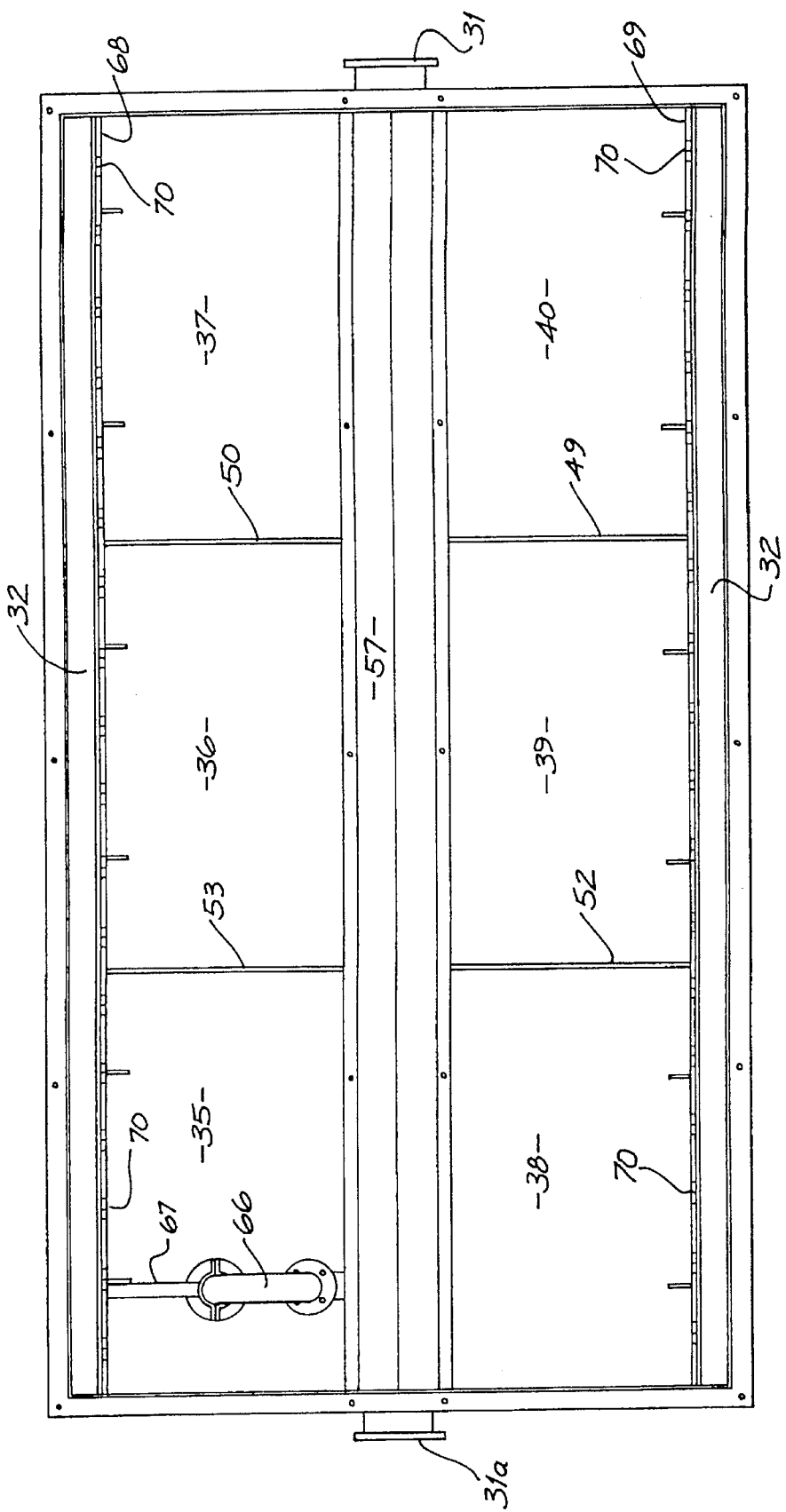
FIG. 10 is a plan view of the top section of the bioreactor of FIG. 1.

A central stiffening flange 16a divides the top section 23 from the bottom section 24 of the vessel 11. A plan view of the top section 23 in isolation is shown in FIG. 10. Plan and front side views of the bottom section 24 in isolation and with the headers 19 and 20 removed and internal tubes removed are shown in FIGS. 6 and 7.

Drain ports 21 located on both side walls 13 and 14 allow the draining of liquid and the removal of bed particles from the vessel 11.

The vessel 11 rest on a series of stands 25 connected to the vessel floor 22. The floor 22 has drain channels 22a, shown in FIG. 5, that lead to the drain ports 21.

Figure 5:
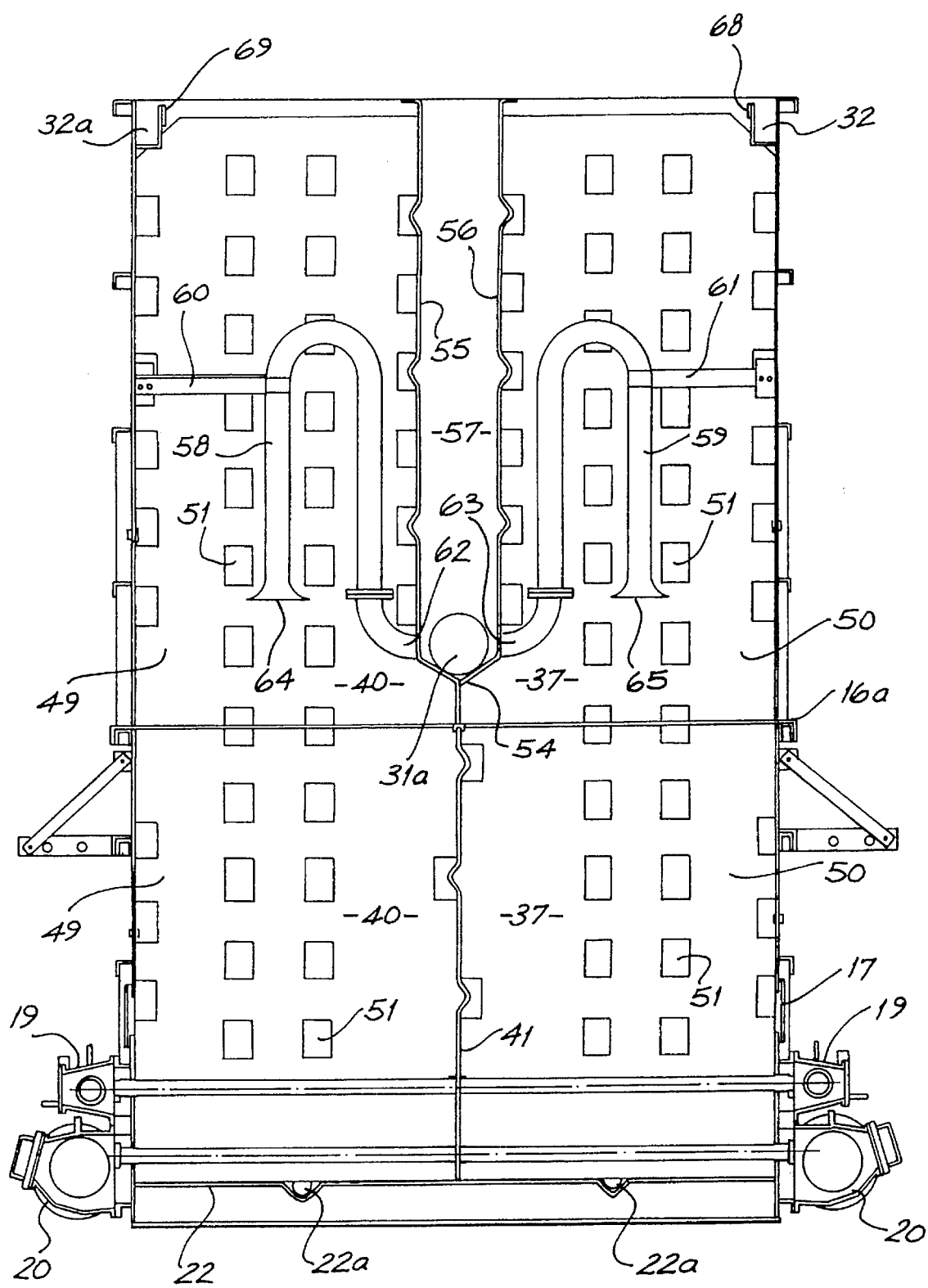
FIG. 5 is a sectional view taken in the direction of arrows BB of FIG. 2.

The vessel 11 is divided into six identical treatment compartments or cells 35, 36, 37, 38, 39, and 40 that are separated by dividing walls shown in FIGS. 5 and 10.

Figure 11:
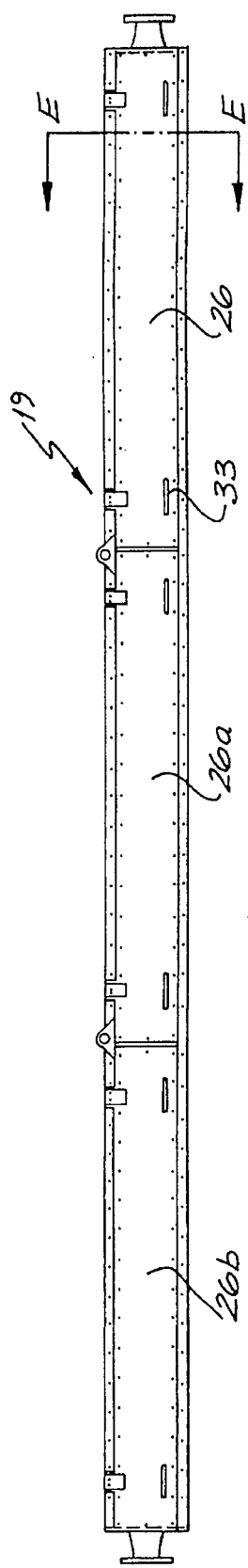
FIG. 11 is a side elevational view of an air supply header for the bioreactor of FIG. 1.

The air supply header 19 and liquid flow header 20 are shown in FIG. 1 providing access to a plurality of vessel air supply tubes 28 that communicate with the main header air supply cavity 43 and the vessel liquid collector tubes 29 that communicate with the main header liquid flow cavity 44 defined within their respective headers. FIG. 11 shows the air supply header 19 in isolation.

Backwash exit ports 31 and 31a are located at both side walls 13 and 14 and communicate with the interior of the vessel 11 through a trough and syphon arrangement located in the top section 23 of the vessel. The trough and syphon arrangement is described in more detail with reference to FIGS. 5 and 10.

Liquid feed troughs 32 and 32a extend along the length of the opposed inside upper ends of the vessel 11. The liquid feed troughs 32 and 32a are described in more detail with reference to FIGS. 5 and 10.

Figure 4:
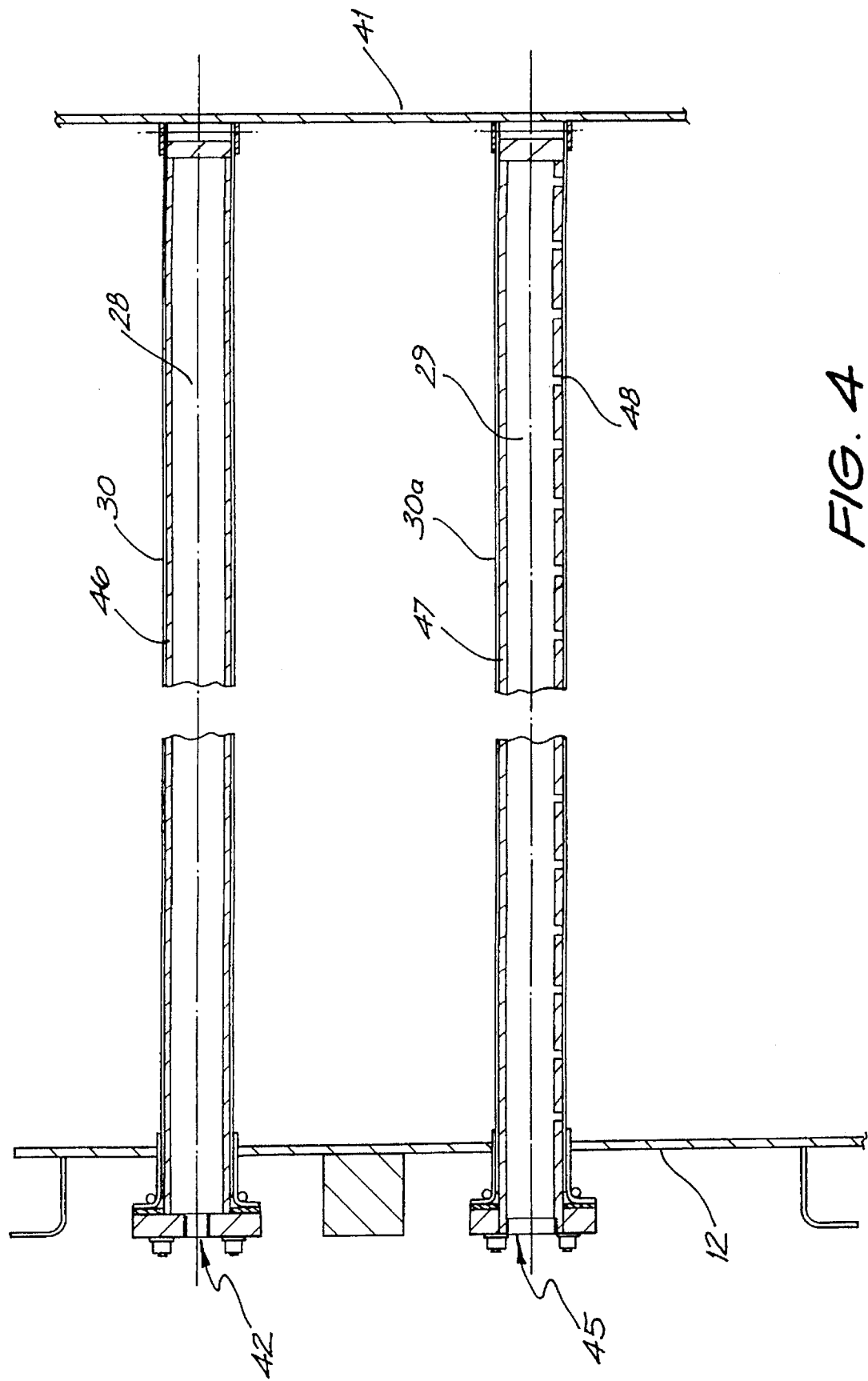
FIG. 4 is a sectional view taken in the direction of arrows AA of a part of the bioreactor shown in FIG. 2.

FIG. 4 shows a longitudinal cross-sectional view of an individual vessel air supply tube 28 and an individual vessel liquid collector tube 29. Both tubes are close ended against the central dividing wall 41. Vessel air supply tube 28 has an opening 42 to the main header air supply cavity 43 within the air supply header 19. Vessel liquid collector tube 29 has an opening 45 to the main header liquid flow cavity 44.

Each of the vessel air supply tubes 28 and vessel liquid collector tubes 29 is enclosed in a stainless steel mesh coal particle shield 30 and 30a respectively (shown in cross sectional detail in FIG. 4).

For the vessel air supply tubes 28, the particle shield 30 is enclosed around an inner tube 46 of microporous polyethylene. Air is able to pass through the pores of the polyethylene tube 46 and the mesh shield 30. For the vessel liquid collector tubes 29, the particle shield 30a is enclosed around an inner tube 47 made of ABS polymer. The inner tube 47 has a series of arcuate slits 48 spaced about 40 mm apart along its length that are cut part-circumferentially around its lower portion. Each slit 48 has an opening width of about 0.5 mm.

FIG. 5 shows a sectional view through the vessel 11 to reveal the interior of the compartments 40 and 37. These compartments are separated from each other by the wall 41 and are separated from the compartments 39 and 36 respectively, which are behind them, by dividing walls 49 and 50. Walls 49 and 50 are perforated by holes 51 that enable the compartments 40 and 37 to be in liquid communication with compartments 39 and 36 respectively, which in turn are in liquid communication with compartments 38 and 35 respectively through similar holes in walls 52 and 53. The dividing wall 41 between the set of compartments 35, 36 and 37 and the set of compartments 38, 39 and 41 does not have any perforations and therefore these two sets of compartments are not in liquid communication with each other and can operate independently of each other.

The central dividing wall 41 has a bifurcation point 54 where the wall 41 divides into subwalls 55 and 56. The subwalls 55 and 56 of wall 41 define a trough 57 therebetween. The trough 57 has exit ports 31 and 31a through the side walls 13 and 14 respectively.

Located in the top section of each vessel compartment are a pair of syphons. Syphons 58 and 59 of compartments 40 and 47 respectively are shown in FIG. 5. Each siphon 58 and 59 is supported by a clamp arm 60 and 61 respectively mounted to the front and rear vessel walls respectively. Each syphon 58 and 59 has a trough opening 62 and 63 respectively through the subwalls 55 and 56 respectively against which subwalls the syphons are also supported. At the other end of each syphon 58 and 59 is a bell mouth opening 64 and 65 respectively.

The bed particles are packed to a height about 100 to 200 mm below the bell mouth openings 64 and 65

FIG. 10 shows a top view of a syphon 66 located in compartment 35 supported by clamp arm 67.

Although not shown in FIG. 10, each compartment has two syphons.

The liquid feed troughs 32 and 32a shown in FIGS. 5 and 10 are closed at both ends. Each trough 32 and 32a has an upstanding knife edge wall 68 and 69 respectively over which liquid feed filling each trough is adapted to spill into the vessel 11.

The walls 68 and 69 have spaced apart V-shaped notches 70 that regulate the volume of liquid feed that will spill into the vessel 11.

Liquid feed is fed into the troughs 32 and 32a through hose pipes (not shown) having their outlets resting within the troughs.

The vessel bottom section 24 shown in FIGS. 6 and 7 has had the headers 19 and 20 and vessel air supply tubes 28 and vessel liquid collector tubes 29 removed therefrom. The lifting beams 18 have also been removed. The openings in the front wall 12 adapted to communicate between the main header air supply cavity 43 and the plurality of vessel air supply tubes 28 are shown as openings 42a. The openings in the front wall 12 adapted to communicate between the main header liquid flow cavity 44 and the plurality of vessel liquid collector tubes 29 are shown as openings 45a.

Figure 8:
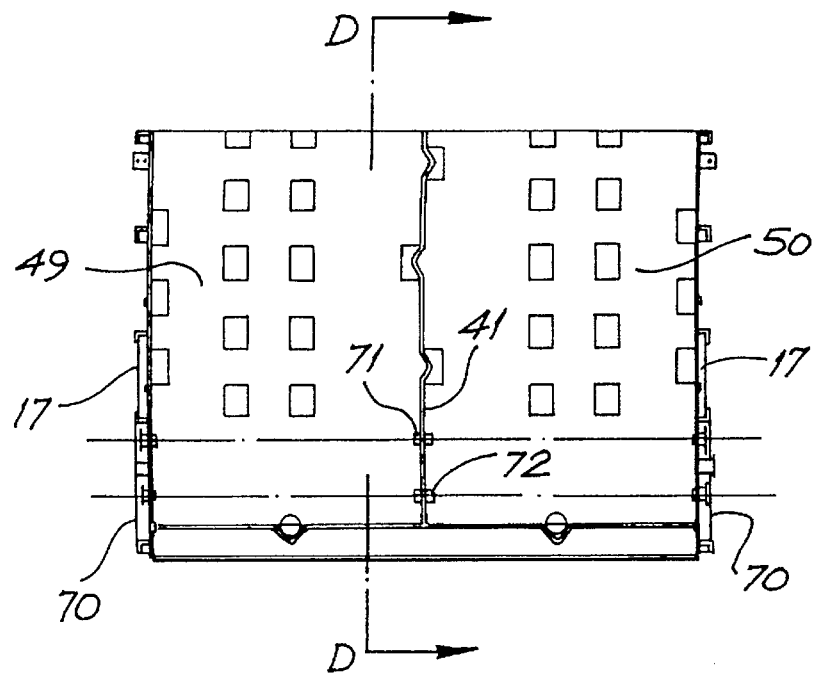
FIG. 8 is a sectional view taken in the direction of arrows CC of FIG. 7.

FIG. 8 shows a sectional view through the bottom section 24 of FIG. 7 to reveal the dividing walls 41, 49 and 50 and holes 51 therein. Also shown are the wall flanges 70 for both of the headers 19 and 20, and sight glasses 17.

Figure 9:
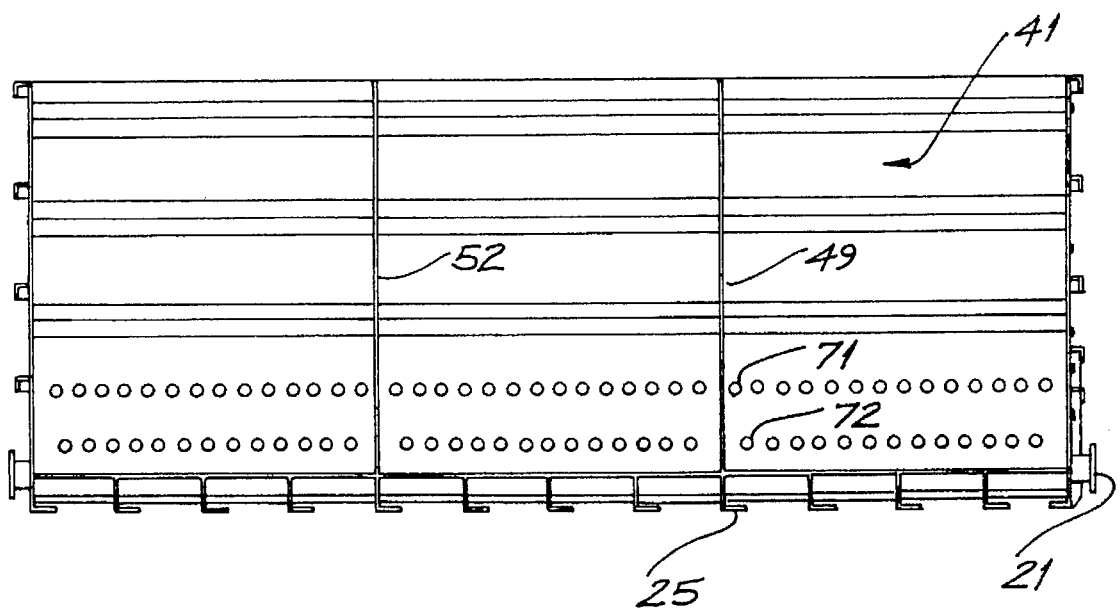
FIG. 9 is a sectional view taken in the direction of arrows DD of FIG. 8.

FIG. 9 shows a sectional view through the bottom section 24 of FIG. 8 to reveal the dividing walls 41, 49 and 52. Receiving pipes 71 extending from the wall 41 are adapted to support the ends of the vessel air supply tubes 28. Similar receiving pipes 72 are adapted to support the ends of the vessel liquid collector tubes 29.

Figure 12:
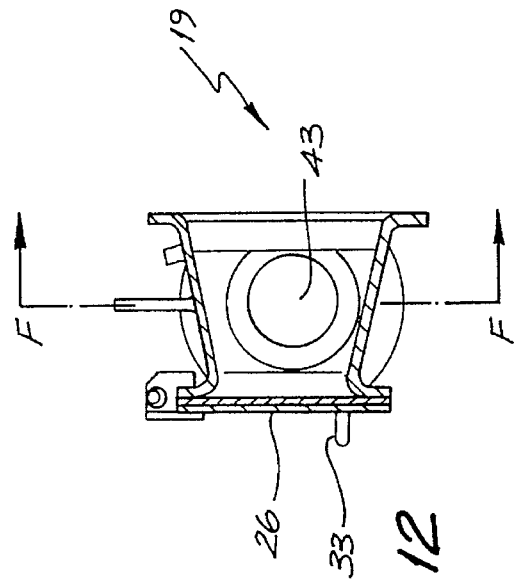
FIG. 12 is a sectional view taken in the direction of arrows EE of FIG. 11.
Figure 13:
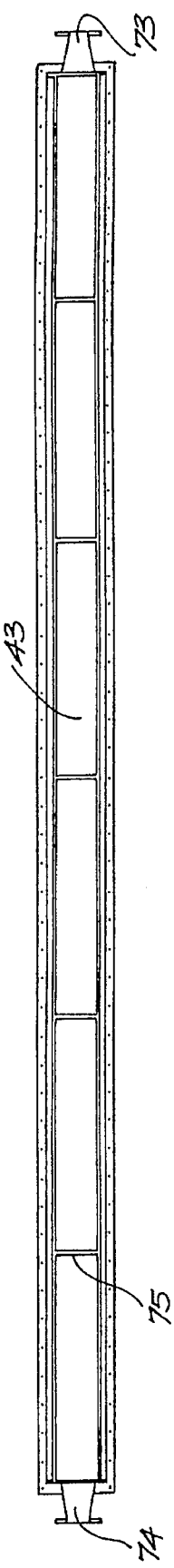
FIG. 13 is a sectional view taken in the direction of arrows FF of FIG. 12.

The air supply header 19 shown in isolation in FIG. 11 has three hinged covers 26, 26a and 26b and handles 33 and is shown sectionally in FIGS. 12 and 13. The main header air supply cavity 43 defined within the header 19 has end openings 73 and 74 and stiffeners 75.

The liquid flow header 20 shown in isolation in FIG. 14 also has three hinged covers 27, 27a and 27b and handles 34 and is shown sectionally in FIGS. 15 and 16. The main header liquid flow cavity 44 defined within the header 20 has end openings 76 and 77 and stiffeners 78.

The packed bed of coal particles within the bioreactor vessel 11 supports the growth of microorganisms preferably derived from the sewage or other feed to be treated. The microorganisms digest nutrient in the feed and, as a result, reduce BOD and COD. The growth of the microorganisms on the particulate material forms a film of microorganisms or biofilm on the particles.

During normal operation, the microorganisms in the bed are supplied with respiratory or process air containing oxygen that is introduced under slight pressure through the main header air supply cavity 43 and then into the series of vessel air supply tubes 28 from where it escapes into the vessel 11 through the pores of the microporous polyethylene material making up the tubes 28. The process air enters the main header air supply cavity 43 through one end thereof only (shown by arrow A in FIG. 1) and the opposite end is closed by an appropriate valve mechanism (not shown) to allow build up of the desired pressure.

At predetermined intervals, pulse air is introduced under higher pressure through the opposite end (shown by arrow B in FIG. 1) of the main header air supply cavity 43 to that used for introducing process air. The now opposite end is closed by an appropriate valve mechanism (not shown) to enable the required pulse pressure to be generated.

During normal operation, treated effluent leaves the vessel 11 by passing through the slots 48 into the vessel liquid collector tubes 29, passing through the tubes 29 to the main header liquid flow cavity 44 and then leaving the cavity 44 in the direction of arrow C shown in FIG. 1. The opposite end of the cavity 44 is closed by an appropriate valve mechanism (not shown).

At predetermined intervals, treated effluent is backwashed into the vessel 11 through the slots 48. The backwash liquid enters the main header liquid flow cavity 44 in the direction of arrow D shown in FIG. 1, before passing to the vessel liquid collector tubes 29 from where it is expelled into the vessel 11. During the backwash operation, the opposite end of the cavity 44 is closed by an appropriate valve mechanism (not shown).

Figure 17:
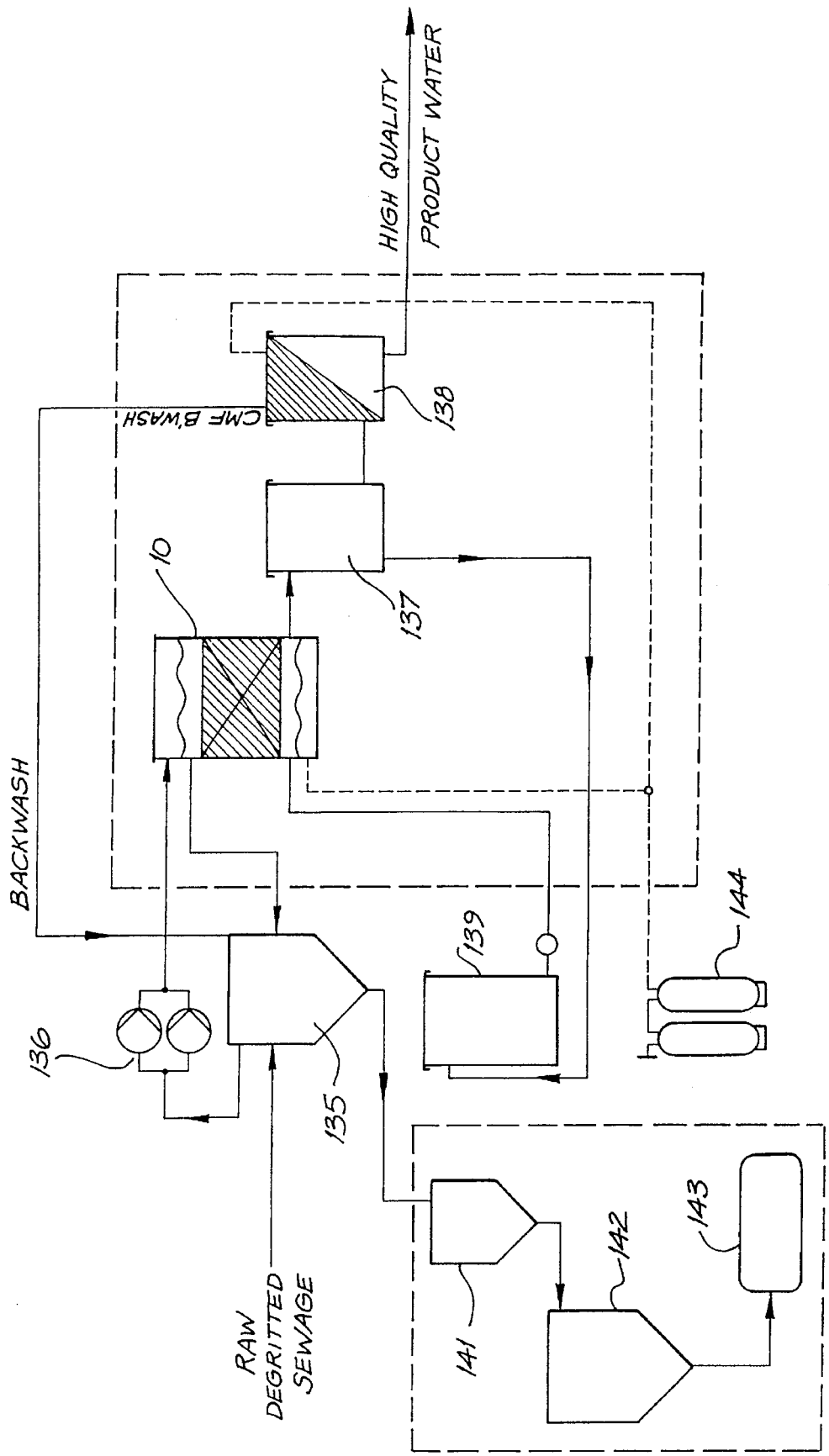
FIG. 17 is a schematic diagram of a sewage treatment plant utilizing the bioreactor of FIG. 1.

The operation of the bioreactor 10 in the sewage treatment plant depicted schematically in FIG. 17 will now be described.

Raw degritted sewage passes into a primary setting tank 135 and allowed to settle. The supernatent therefrom is pumped by feed pumps 136 through hose pipes into the feed troughs 32 and 32a of the bioreactor 10 from where it spills onto the liquid already submerging the bed.

The bioreactor vessel contains a bed of coal particles 2.8 m in height, giving an effective bed volume of 56 m³. The bed is submerged in 26 m³ volume of sewage which during normal operation is at a height of between 0.1 to 1.2 m above the bed. The ratio of void volume to coal volume of the bed is about 0.4. The sewage temperature is 20° C.

During normal treatment operation, sewage flow rate through the bioreactor is 100 m³/hr. The countercurrent respiratory air flow rate is 240 m³/hr.

The metabolic activity of the microorganisms leads to cell growth and proliferation through rapid asexual division and this, in turn, leads to an increase in the thickness of the biofilm on the bed particles.

In order to limit the growth of the biofilm to a thickness where the microorganisms comprising the biofilm do not clog the bed, the bed is periodically subjected to an upward air pulse.

This normal treatment operation was continued for 60 minutes, whereafter sewage feed and respiratory air flow was stopped in compartments 38, 39 and 40 but continued in compartments 35, 36 and 37. A 2 second delay follows to allow valves to close.

In compartments 38, 39 and 40, an air pulse lasting 3 seconds at 70 kPa pressure was then passed through the bed. This was followed by a second identical air pulse 8 seconds later. During each air pulse, 5000 liters of air was injected into the bed. After the second pulse, sewage feed and respiratory air flow in compartments 38, 39 and 40 were resumed at the previous rates for another 60 minutes until the pulse operation was repeated. Air pulsing was also carried out in compartments 35, 36 and 37 with the same parameters as above but at different times to the pulsing of compartments 38, 39 and 40 so that all six compartments are not pulsed simultaneously.

The cycles of treatment operation and pulsing were continued for a period of 8 hours until commencement of the backwashing operation whereupon the treatment operation in compartments 35, 36 and 37 was stopped. An air pulse identical to previous pulses was then pulsed through the bed, 12,000 liters of filtrate from the bioreactor was pumped backed into the compartments 35, 36 and 37 at a flow rate of 380 m³/hr. For the first 80 seconds successive mini-pulses of air were pumped into the se compartments as before but of only 1 second duration and spaced 10 seconds apart.

After the pumping of the filtrate and succession of mini-pulses has ceased the respiratory air is restored for 60 seconds. This restores air to the bed and ensures that the particles in the bed repack to form the bed. The respiratory air is then removed and a further 40 second settling period allows coal particles that have been suspended in the backwash effluent to settle. After the settling period, the sewage feed is reapplied for a period of 30 seconds until the syphon operation starts.

The backwash liquor is then removed through the syphons from the top of the bioreactor. This syphoning process was completed within 135 seconds whereafter normal treatment operation and pulse cycles were resumed. The entire backwashing operation took 6 minutes 34 seconds in this instance.

During normal treatment, the treated sewage that leaves the bed through the slots 48 passes via the header 20 to a balancing tank 137 before being filtered by a continuous microfiltration unit (CMF) 138 operated according to Australian Patents 563,321 and 576,424. The teachings of Australian Patents 563,321 and 576,424 are incorporated herein by reference.

Clear, disinfected water is produced after the further treatment by the CMF. Liquid from the balancing tank 137 may be diverted to the storage tank 139 to be used in the bioreactor backwash. Solids collected on the membrane filter not shown) of the CMF unit 138 would periodically be removed, by the CMF backwash, to the settling tank 135 and supernatent liquid would then be pumped into the bioreactor 10. The backwash of the CMF 138 is effected primarily by using air blowback.

In backwashing shed biomass from the bioreactor 10 the backwash liquid is pumped in at the bottom of the bioreactor 10 and liquid carrying shed biomass is collected through the siphons at the top of the bioreactor 10. The solids thus collected are settled for a given period in settling tank 135. The settled solids are then sent to a sludge thickener 141 and a dewatering plant 142 for further concentration and processing into stable sludge 143, whereas the clearer liquid taken from the settling tank 135 is ultimately recycled back to the bioreactor 10. Air for respiratory, pulse and backwash operations of the bioreactor 10 and for blowback of the CMF 138 is supplied by an air delivery system 144.

In the present invention the frequency at which pulsing is effected is greater than in prior art systems which, in the main, have focused on long term stability of the bed for relatively uninterrupted microbiological metabolic activity. As foreshadowed earlier, the bioreactor beds of the prior art rapidly become clogged by biomass as uninterrupted biofilm growth bridges the gaps between bed particles and leads to longer sewage residence times.

The effect of the periodic pulsing with air in the present invention is to reorientate or mix the bed particles, so removing any channelling effects on respiratory air or the sewage stream. As channelling may lead to preferential passage of nutrient to some areas of the bed only, whilst leaving other areas of the bed starved of nutrient, with the result that the effective bioreactor bed volume is reduced, elimination of channelling effects is an important element in the efficient operation of any bioreactor.

The importance of the explosive pulsing regime in controlling sewage flow rate through the bioreactor of the invention by maintaining an unclogged bed is shown in the following example. The example was carried out using two 6 inch diameter cylindrical trial bioreactors in parallel to determine the effect of pulse and no pulse on bioreactor performance. The intention of the trial was that the only difference between the operation of the two bioreactors would be the pulse and no pulse.

A media depth of 3 meters was used. The coal media used as the biofilm support media had an effective size of 2.3–2.5 mm with a uniformity coefficient of 1.5.

These trials were carried out for 25 days. Both bioreactors were backwashed after 8 hours with the pulsed reactor being regularly pulsed every 60 minutes with two short pulses of air through the air supply. These pulses are typically of 3 seconds duration. Normal aeration is from 10–25 m³hr⁻¹ per m² of bed with the pulse air being supplied at 600 m³hr⁻¹ per m² of bed. Temperature of the feed varied from 16°–22° C. The no pulse bioreactor was visibly more difficult to control. After 8 days the backwash needed to be changed and more air used in the backwash in order to keep it running.

Figure 18:
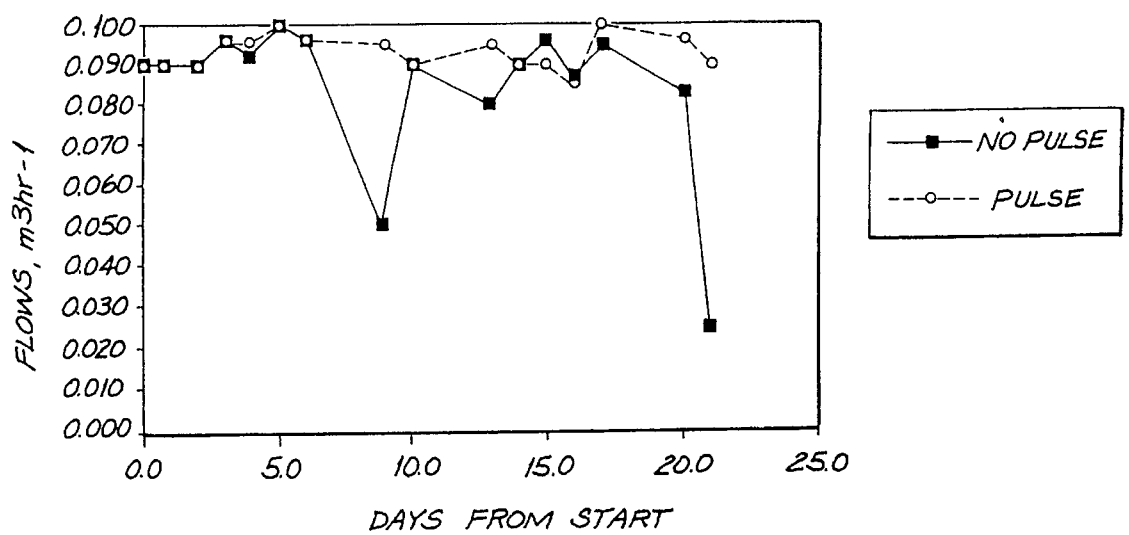
FIG. 18 is a graph of flow rate against time for a bioreactor operated in accordance with the pulsing techniques of the present invention compared with a bioreactor operated without the pulsing techniques.

This can be seen by comparing the flows of the two bioreactors in FIG. 18.

Figure 19:
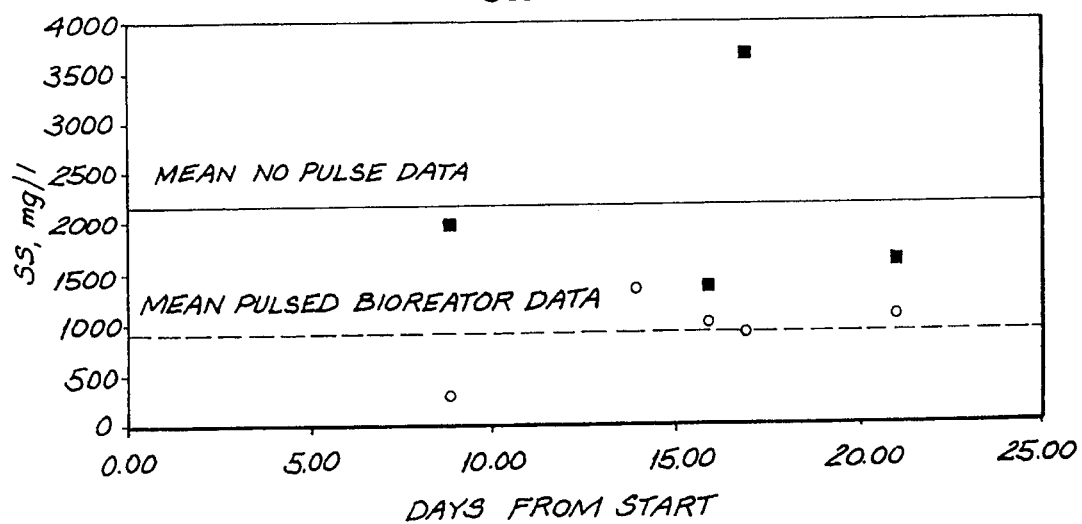
FIG. 19 is a graph of suspended solids concentration against time for a bioreactor operated in accordance with the pulsing techniques of the present invention invention compared with a bioreactor operated without the pulsing techniques.

The biofilm growth on the non pulsing bioreactor was not controlled and so led to a need to have a more vigorous backwash in order to control the media. This can also be seen in the suspended solids in the backwash of the two bioreactors as shown in FIG. 19.

Figure 20:
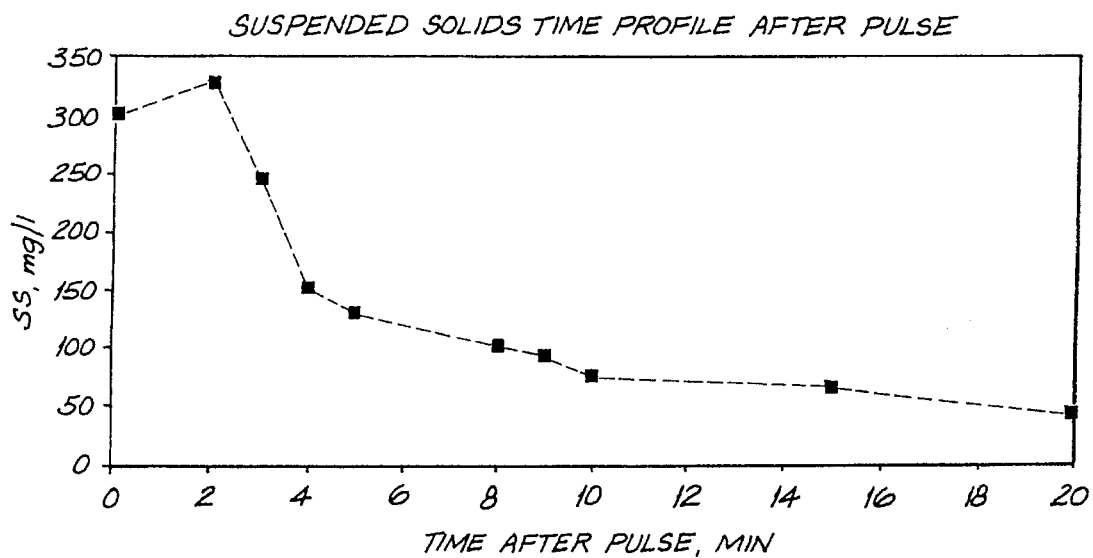
FIG. 20 is a graph of the suspended solids concentration time profile after the bioreactor has been pulsed in accordance with the principles of the invention.

A typical pulse profile of the suspended solids in the effluent is shown in FIG. 20.

The volume of the bioreactor backwash was 35l and so the difference in mass between pulsing and no pulsing is 42 g. In the immediate aftermath of a pulse as shown above 2 g of solid are removed which corresponds to 16 g in a backwash interval. The remainder of the difference will be removed in the rest of the pulse and also due to natural variation.

The storage capacity of the current system being used is calculated at 1.5 kg/m$^3$.

The use of pulsing thus allows control of the residence time of the solids within the bed. Backwash can be reduced but not necessarily eliminated as incoming suspended solids may tend to congregate near the surface of the bed.

Figure 21:
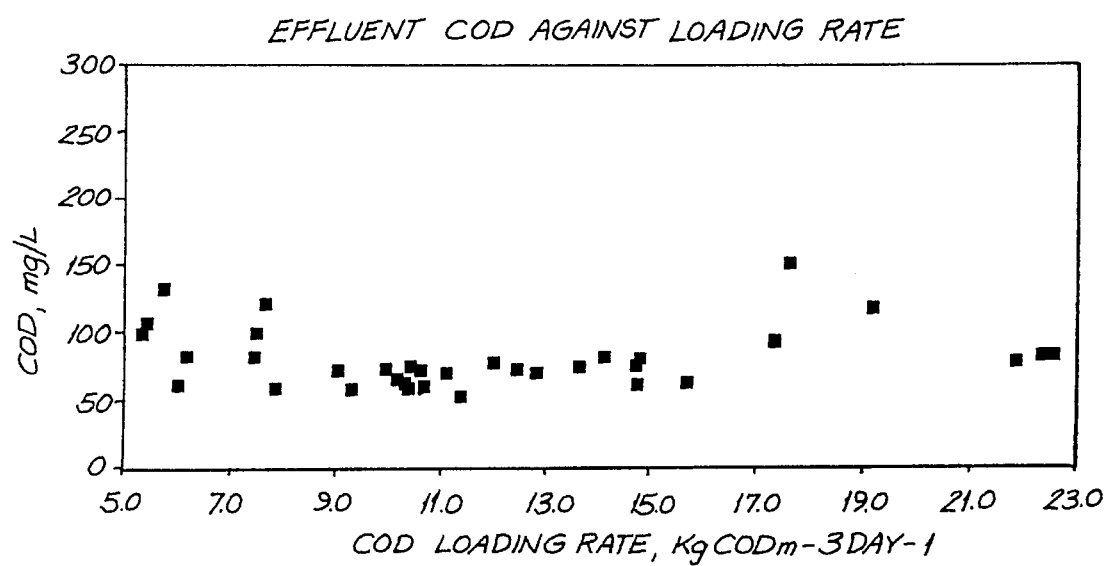
FIG. 21 is a graph of the effluent COD against COD loading rate for a bioreactor operated in accordance with the pulsing techniques of the invention.

A larger surface area per unit volume allows higher loading rates. The loading rates achieved in the bioreactor trial are shown in FIG. 21.

These results compare with unpulsed technology as currently used in the prior art of Australian Patent 528,760 which applies a maximum load of 7 kg CPD/m$^3$.

Figure 22:
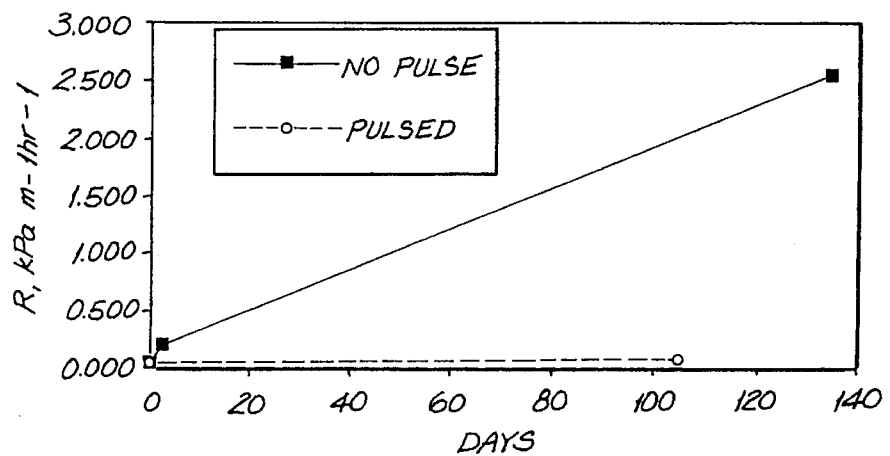
FIG. 22 is a graph of the effluent COD against time for a bioreactor operated in accordance with the pulsing techniques of the invention compared with a bioreactor operated without the pulsing techniques.

Microporous aeration tubes are a good method of distributing air into a bioreactor. They have good distribution properties and produce a fine stream of bubbles. They have however a tendency to become blocked with use. If these are pulsed regularly with air then the tendency to block is reduced. This is shown in FIG. 22.

Various modifications may be made in details of design and construction of the bioreactor and in details of the biological reaction process of the present invention without departing from the scope or ambit of the invention.

We claim:

1. A process for maintaining a high rate of mass transfer of nutrients contained in a liquid feed stream to a biofilm of microorganisms supported on a bed of particulate matter, said process comprising
    A. feeding said microorganisms in said biofilm with a continuous, substantially uniform flow of said liquid feed stream and a countercurrent flow of respiratory air so as to support biofilm growth, and
    B periodically pulsing said bed, while sustaining said continuous, substantially uniform flow of said liquid, with air at a pressure and for a time sufficient to shed at least an increment of said microorganisms from the biofilm and/or to disrupt and rearrange the bed of particulate matter and at intervals sufficient to prevent preferential channelling of the liquid feed stream through the bed.

2. The process of claim 1 wherein the process is interrupted by a liquid backwashing of the bed less frequently than the periodic pulsing.

3. The process of claim 2 wherein the bed is backwashed at intervals of 3 to 24 hours.

4. The process of claim 2 wherein the bed is backwashed for 3 to 7 minutes.

5. The process of claim 2 wherein the bed is backwashed with treated feed stream effluent.

6. The process of claim 1 wherein the respiratory air enters the bed at a pressure of between 20 kPa and 70 kPa.

7. The process of claim 1 wherein the bed is pulsed at intervals of between 20 minutes and 2 hours.

8. The process of claim 1 wherein the bed is pulsed for 1 to 8 seconds.

9. The process of claim 1 wherein the pulsed air enters the bed at a pressure of between 60 kPa and 120 kPa.

10. The process of claim 9 wherein the pressure is 70 kPa.

11. A bioreactor for treating a liquid feed stream to remove nutrient BOD and COD therefrom, comprising:
    A. a vessel containing a bed of particulate matter upon which grow a biofilm of microorganisms that remove nutrient BOD and COD;
    B. means for passing the liquid feed stream downwards through the bed; and
    C. means for passing a continuous uniform flow of respiratory air and for producing a pulsed flow of air upwardly through the bed at a pressure and for a time sufficient to shed microorganisms from the biofilm and/or to disrupt and rearrange the bed of particulate matter, and sufficient to avoid or eliminate preferential channeling of the liquid feed steam through the bed.

12. The bioreactor of claim 11 wherein the means for passing air through the bed includes a plurality of spaced apart porous tubes from which the air passes into the bed.

13. The bioreactor of claim 12 wherein the porous tubes are made of microporous polyethylene.

14. The bioreactor of claim 11 wherein the particulate matter is any coal media having an effective size of 2.3 to 2.5 mm with a uniformity coefficient of 1.5.

15. The bioreactor of claim 11 wherein the bed is a fixed bed and is submerged during the treatment of the liquid feed stream.

16. A liquid feed stream treatment plant comprising the bioreactor of claim 11 and a microfiltration unit to remove solids from the effluent of the bioreactor.

* * * * *